Nov. 12, 1963 L. E. GAVELLO Plant Pat. 2,296
HEBE HYBRID
Filed Aug. 20, 1962
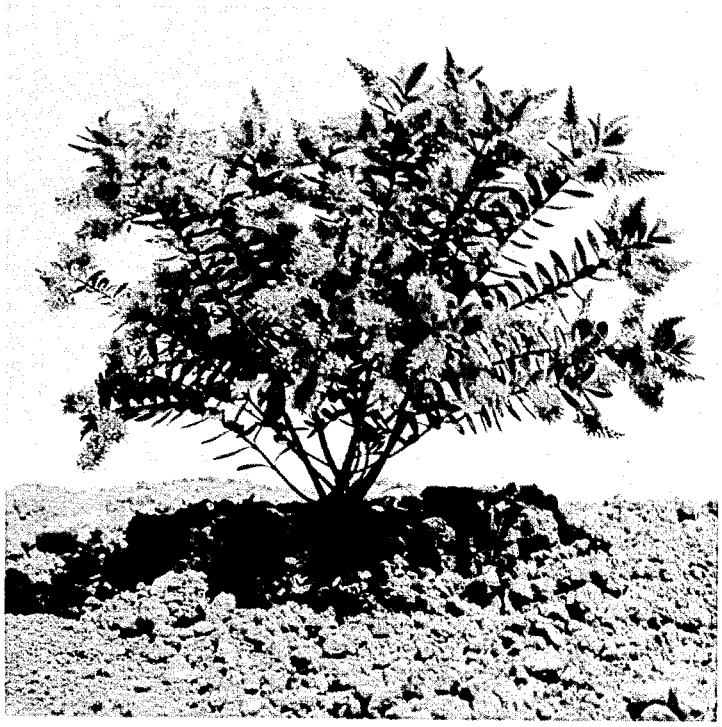
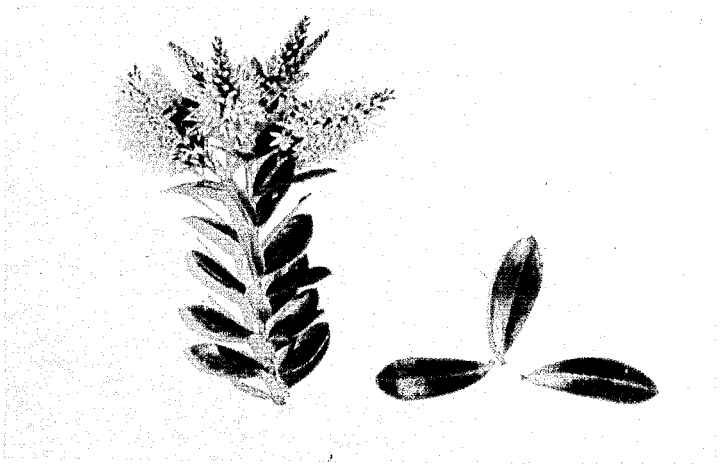
Inventor: LOUIS E. GAVELLO
By Bruce & Brodler
His Attorneys United States Patent Office Plant Pat. 2,296
Patented Nov. 12, 1963

2,296

HEBE HYBRID

Louis E. Gavello, 3438 Maricopa Ave., Richmond, Calif.

Filed Aug. 20, 1962, Ser. No. 218,189
1 Claim. (Cl. Plt.—54)

My invention relates to a new and distinct variety of Hebe (Veronica) of shrub type which was initially originated by me as a selective hybrid seedling and thereafter effectively reproduced by me from cuttings at Richmond, California.

My new shrub is a cross between *Hebe elliptica* and *Hebe speciosa*.

The parent *Hebe elliptica*, as grown in California, is generally seen as a shrub approximately five feet tall with pale purplish white flowers, and pale green foliage which is broader and longer than the hybrid of the present invention.

The other parent, *Hebe speciosa*, is a shrub growing to five feet in height with reddish-purple flowers, and large dark green foliage which has reddish coloration to the petiole, leaf margin and midrib.

The major distinctions of the hybrid of the present invention over the parent plants are primarily that of color of the flower, form of raceme, and foliage. The flowers are bright purple pink in color and are carried in great profusion on the outside tips of all branches. The foliage is clear dark green in color, with leaves smaller and arranged in a one-sided effect rather than being evenly symmetrical around the stem as in the parent plants.

A secondary distinction of this new variety over the parent plants resides in the fact that the new plant is loosely compact whereas the parent plants are densely compact.

The hybrid of the present invention grows well in windy areas, particularly in areas where salt spray is a problem. It will grow in sun or shade and will take all exposures. It can be pruned and recovers quickly from damage which may occur, filling in rapidly due to its ability to break new growth from old wood. It is a rapid growing plant.

The following specific description of this new hybrid as to color of flowers and foliage is keyed to plate numbers to be found in Dictionary of Color, 1950 by Maerz and Paul.

*Hebe (Hybrid)*

Growth habit:

(1) Height—about 4 feet.
(2) Spread—about 5½ feet–6 feet.

(3) Loosely compact habit, much branched shrub from the base, with branches rising evenly from horizontal to vertical position from the crown to form a plant of even and rounded outline, slightly wider than high.
(4) The foliage pattern is in two ranks on the stem to give a symmetrical pattern with a wide trough effect along the upper side of the stems as seen from above. This gives it something of the foliage character of *Hebe menziesi*.
(5) Highly floriferous plant, blooming from April through October with occasional bloom through the winter with two major periods of bloom, one in May and one in August.

Leaves:

(1) Evergreen, glabrous, smooth, thick, elliptic obovate, narrowing toward petiole.
(2) Color—Bakst Green (Plate 31—E–12) (p. 85).
(3) Length of leaves—1⅛ inches to 1½ inches—older foliage to 1½ inches and usually carried on the inside portion of the plant.
(4) Width—⅜ inch to ½ inch at widest portion.
(5) Petiole—short petioled—⅛ inch long.
(6) Leaf arrangement—opposite.
(7) Leaf margins—entire.

Flowers:

(1) Color—bright purple with reddish-pink undertones described technically as Lithe Purple (Plate 44—I–8 and Plate 44—H–8 and J–9) (p. 111). Uniform color for petals, with white throat.
(2) Flower buds of similar color.
(3) Flowers are held in compact axillary compound racemes 1½ inches long, near the tips of the branches; conical-shaped racemes approximately 1 inch across at the base in flower and tapering to point at the tip. Approximately 30 to 40 flowers per raceme.
(4) Petals—¼ inch long including a type about 1/16 inch long. Spread of petals—⅜ inch.
(5) Bright purple stamens protruding about ¼ inch beyond petals.

Having thus described my invention and discovery, I claim:

A new and distinct variety of Hebe (Veronica) plant substantially as herein described and characterized particularly by bright purplish-pink flowers carried in profusion in compound racemes on the outside tips of its branches.

No references cited.